(12) United States Patent
Xiao et al.

(10) Patent No.: US 11,939,440 B2
(45) Date of Patent: Mar. 26, 2024

(54) ALCOHOL SOLUBLE PROTEIN GAS-LIQUID INTERFACE SELF-ASSEMBLED POROUS MEMBRANE AND PREPARATION METHOD THEREOF

(71) Applicant: SOUTH CHINA AGRICULTURAL UNIVERSITY, Guangdong (CN)

(72) Inventors: Jie Xiao, Guangdong (CN); Wuhui Lu, Guangdong (CN); Jiyang Cai, Guangdong (CN)

(73) Assignee: SOUTH CHINA AGRICULTURAL UNIVERSITY, Guangdong (CN)

( * ) Notice: Subject to any disclaimer, the term of this patent is extended or adjusted under 35 U.S.C. 154(b) by 0 days.

(21) Appl. No.: 18/029,103

(22) PCT Filed: Aug. 31, 2022

(86) PCT No.: PCT/CN2022/116283
§ 371 (c)(1),
(2) Date: Mar. 29, 2023

(87) PCT Pub. No.: WO2023/077935
PCT Pub. Date: May 11, 2023

(65) Prior Publication Data
US 2023/0295386 A1    Sep. 21, 2023

(30) Foreign Application Priority Data

Nov. 8, 2021  (CN) .......................... 202111315081.0

(51) Int. Cl.
*C08J 5/22* (2006.01)
*B01D 67/00* (2006.01)
(Continued)

(52) U.S. Cl.
CPC .  *C08J 5/18* (2013.01); *C08J 9/28* (2013.01); *A61M 31/002* (2013.01);
(Continued)

(58) Field of Classification Search
None
See application file for complete search history.

(56) References Cited

U.S. PATENT DOCUMENTS 5,456,941 A    10/1995    Takahashi et al.

FOREIGN PATENT DOCUMENTS

| CN | 104387604 | 3/2015 |
|----|-----------|--------|
| CN | 110218353 | 9/2019 |

(Continued)

OTHER PUBLICATIONS

"International Search Report (Form PCT/ISA/210) of PCT/CN2022/116283," dated Dec. 5, 2022, pp. 1-4.

*Primary Examiner* — Richard A Huhn
(74) *Attorney, Agent, or Firm* — JCIPRNET (57) ABSTRACT

An alcohol soluble protein gas-liquid interface self-assembled porous membrane and a preparation method thereof are provided. The alcohol soluble protein gas-liquid interface self-assembled porous membrane is prepared from an alcohol soluble protein membrane storage solution by an anti-solvent method. The porous interface membrane is rapidly prepared by an alcohol soluble protein interface self-assembled one-step method and can be rapidly formed within 4 seconds, which greatly improves the preparation efficiency of the alcohol soluble protein membrane. The structure (size, pore diameter, micro porosity) of the alcohol soluble protein interface self-assembled porous membrane is precisely regulated and controlled by regulating and controlling process parameters, and a new preparation solution of an alcohol soluble protein base membrane, which is more efficient and has a modifiable structure compared with an alcohol soluble protein membrane prepared by a traditional solvent evaporation method, is developed.

4 Claims, 8 Drawing Sheets

(51) Int. Cl.
*C08J 5/18* (2006.01)
*C08J 9/28* (2006.01)
A61M 31/00 (2006.01)
B01D 69/00 (2006.01)

(52) U.S. Cl.
CPC .......... *B01D 67/0002* (2013.01); *B01D 69/00* (2013.01); *C08J 5/2212* (2013.01); *C08J 2389/00* (2013.01)

(56) References Cited

FOREIGN PATENT DOCUMENTS

| | | | |
|---|---|---|---|
| CN | 114085415 | | 2/2022 |
| CN | 114085415 A | * | 2/2022 |
| CN | 114099475 | | 3/2022 |
| CN | 114099475 A | * | 3/2022 |

* cited by examiner

ALCOHOL SOLUBLE PROTEIN GAS-LIQUID INTERFACE SELF-ASSEMBLED POROUS MEMBRANE AND PREPARATION METHOD THEREOF

This is a 371 application of the International PCT application serial no. PCT/CN2022/116283, filed on Aug. 31, 2022, which claims the priority benefits of China Application No. 202111315081.0, filed on Nov. 8, 2021. The entirety of each of the above-mentioned patent applications is hereby incorporated by reference herein and made a part of this specification.

TECHNICAL FIELD

The present invention belongs to the technical field of protein membrane preparation, and in particular, relates to an alcohol soluble protein gas-liquid interface self-assembled porous membrane and a preparation method thereof.

DESCRIPTION OF RELATED ART

China is a large country of grain, and by-products of grain processing contain rich protein. However, most of cereal protein is used as animal feed and crop fertilizers at low value, or is treated as waste during the processing of agricultural and sideline products such as fermentation and oil pressing. About 40% of cereal protein is made into waste every year, causing environmental pollution and resource waste. The development of cereal alcohol soluble protein based deep-processing products to increase the added value of agricultural and sideline products is the current research focus in the field of deep processing of agricultural products. As an important component of cereal protein, alcohol soluble protein, such as gliadin, zein, kafirin, hordein, etc., usually accounts for 40% to 80% of the total cereal protein. The cereal alcohol soluble protein contains 40% to 60% hydrophobic amino acids as well as many sulfur-containing amino acids such as cysteine, methionine, etc., so it shows unique characteristics of self-assembly, membrane forming, gelling, etc.

Traditional technical methods for preparing an alcohol soluble protein membrane mainly include a solvent evaporation, a tape casting method and an electrospinning method. Among them, the solvent evaporation method is the most common, and its preparation process usually includes a method of preparing a protein membrane by pouring a membrane storage solution into a flat plate or other receivers to evaporate a solvent in the membrane storage solution. However, the solvent evaporation method to prepare an alcohol soluble protein base membrane has the disadvantages of long time consuming, poor microstructure modifiability, etc. In addition, there are also many studies on the preparation of an alcohol soluble protein membrane by the tape casting method. For example, Patent CN201410712816.7 provides a high-moisture-resistance biodegradable zein film material and a preparation method thereof, which is formed by zein and a mixed plasticizer under the conditions of tape casting and evaporation, however, the preparation method of this film is complex and long time-consuming, and the film structure is not modifiable.

Therefore, it is very necessary to develop a preparation method of a cereal alcohol soluble protein membrane that can be rapidly formed and has a controllable structure.

SUMMARY

For the shortcomings in the prior art, the present invention aims to provide an alcohol soluble protein gas-liquid interface self-assembled porous membrane and preparation thereof. The porous interface membrane is rapidly prepared by an alcohol soluble protein interface self-assembled one-step method and can be rapidly formed within 4 seconds, which greatly improves the preparation efficiency of the alcohol soluble protein membrane, and the structures such as size, pore diameter, micro porosity, etc. of the interface membrane can be precisely regulated and controlled.

A first purpose of the present invention is to provide a preparation method of an alcohol soluble protein gas-liquid interface self-assembled porous membrane.

Another purpose of the present invention is to provide an alcohol soluble protein gas-liquid interface self-assembled porous membrane prepared by the above method.

A yet another purpose of the present invention is to provide a use of the alcohol soluble protein gas-liquid interface self-assembled porous membrane in preparation of an active substance controlled release product.

The above purposes of the present invention are implemented through the following technical solutions.

The present invention first provides a preparation method of an alcohol soluble protein gas-liquid interface self-assembled porous membrane, including the following steps:

S1. adding an alcohol soluble protein into a good solvent to be dissolved to obtain a membrane storage solution with an alcohol soluble protein concentration of 10 to 30 wt %;

S2. regulating and controlling a temperature of an anti-solvent to be 25° C. to 40° C.; and S3. dropping the membrane storage solution in the S1 into the anti-solvent in the S2 to form a self-assembled porous membrane.

In the above alcohol soluble protein interface membrane one-step preparation method, firstly, the alcohol soluble protein is added into the good solvent to be stirred and dissolved to prepare an alcohol soluble protein membrane storage solution, and then titration is conducted with an anti-solvent, so that the protein rapidly aggregates and diffuses at an interface of the anti-solvent to form a thin membrane with a porous micro interface structure. In which, the cereal alcohol soluble protein has its unique amino acid sequence, and a hydrophobic amino acid content thereof accounts for 50% to 70%, so it has the characteristics of self-assembly and membrane forming at a gas-liquid interface. The interaction force between protein molecules is regulated and controlled by regulating and controlling the concentration of the cereal alcohol soluble protein. When the protein concentration is too low, the hydrophobic interaction force between the protein molecules in the membrane storage solution is small, so a continuous thin membrane cannot be formed. When the protein concentration is too high, there are more proteins in the membrane storage solution, the probability of collision increases, the hydrophobic interaction force between the protein molecules increases, the solution is not easy to diffuse at the interface, so a formed thin membrane has a small diameter and long film forming time, or a thin membrane cannot be formed due to poor diffusion performance. The concentration of the alcohol soluble protein will affect the self-aggregation of proteins at the interface and the diffusion effect of the solvent, thus changing the morphology and structure of upper and lower surfaces of the interface membrane, such as a porous structure, hydrophilicity and hydrophobicity, etc. In addition, the self-assembly and diffusion processes of the alcohol soluble protein at the gas-liquid interface are further regulated and controlled by regulating and controlling the temperature of the anti-solvent, so that interface membranes with different microstructures are obtained, which is a new solution that can improve the efficiency of film forming and prepare alcohol soluble protein membranes with different micro porous structures.

Preferably, the dissolution in the S1 is stirring and ultrasonic to complete dissolution.

Preferably, pH of the anti-solvent is 3.0 to 10.0, and an ionic strength thereof is 0 to 700 mM.

The inventor's targeted research results show that when the pH of the anti-solvent is too low, the protein molecules will be quickly self-assembled, so a formed thin membrane has a small diameter and long film forming time, or a thin membrane cannot be formed due to its too fast aggregation; when the pH of the anti-solvent is too high, the solubility of the protein molecules in the anti-solvent is increased, causing the diffusion time is prolonged, so a formed thin membrane has a large diameter and uneven thickness, or a thin membrane cannot be formed due to its too fast diffusion.

When the ionic strength of the anti-solvent is too low, external ions will compete for a hydration layer of an outer layer of the protein, the interaction force between the protein molecules increases, so the self-aggregation degree of the protein is increased; when the ionic strength of the anti-solvent is too high, salt ions will combine with carboxyl and amino groups on the protein, so that the amount of charge of the protein molecules is reduced, so the self-aggregation degree of the protein molecules is decreased; and the diameter of a formed thin membrane is too large or too small, or a thin membrane cannot be formed due to its too fast and too slow diffusion and self-aggregation.

The pH of the anti-solvent can be regulated by sodium hydroxide and/or hydrogen chloride. The ionic strength of the anti-solvent can be regulated by sodium chloride. The morphology and structure of the membrane can be regulated and controlled by regulating and controlling the temperature, pH and ionic strength of the anti-solvent.

Further preferably, the pH of the anti-solvent is 3.0 to 9.0, and an ionic strength thereof is 50 to 500 mM.

Preferably, the alcohol soluble protein includes, but is not limited to, any one of gliadin, zein, kafirin and hordein.

Preferably, the good solvent in the S1 includes any one of an aqueous ethanol solution, an aqueous methanol solution, an aqueous acetic acid solution and an aqueous acetone solution. Further preferably, the good solvent includes 50% to 90% (v/v) of the aqueous ethanol solution, 60% to 90% (v/v) of the aqueous methanol solution, 60% to 100% (v/v) of the aqueous acetic acid solution and 70% to 90% (v/v) of the aqueous acetone solution.

Preferably, the good solvent includes any one of water, an aqueous ethanol solution, an aqueous methanol solution, an aqueous acetic acid solution and an aqueous acetone solution. Further, the anti-solvent includes any one of water, 0.1% to 50% volume fraction of the aqueous ethanol solution, 0.1% to 60% volume fraction of the aqueous methanol solution, 0.1% to 60% volume fraction of the aqueous acetic acid solution and 0.1% to 70% volume fraction of the aqueous acetone solution. More further, a volume fraction of the aqueous ethanol solution is 10% to 30%, a volume fraction of the aqueous methanol solution is 10% to 30%, a volume fraction of the aqueous acetic acid solution is 10% to 30%, and a volume fraction of the aqueous acetone solution is 10% to 40%.

Preferably, titration of the anti-solvent in the S3 is single titration, and a volume ratio of the alcohol soluble protein membrane storage solution to the anti-solvent during titration is 1:(500 to 10,000), most preferably 1:1,000. When the amount of the anti-solvent is too small, the diffusion in the anti-solvent of the good solvent in the membrane storage solution will affect the aggregation and diffusion of the interface membrane during the titration; and when the amount of the anti-solvent is too high, the cost of the product increases. In the process of anti-solvent titration, a mould can be used to prepare an interface self-assembled porous membrane with the same shape as the mould.

The alcohol soluble protein gas-liquid interface self-assembled porous membrane prepared by the above method also falls within the scope of protection of the present invention.

Preferably, a pore diameter of the porous membrane prepared according to the above method is 0.1 to 30 µm, and a porosity thereof is 10% to 80%. Since the self-aggregation of the alcohol soluble protein at the gas-liquid interface and the diffusion of the anti-solvent are sensitive to temperature, pH, ionic strength and the concentration of the good solvent, the controllability of the microscopic morphology and structure of the cereal alcohol soluble protein membrane can be achieved by regulating and controlling the temperature, pH and ionic strength of the anti-solvent and the concentration of the good solvent.

Based on the self-assembly characteristic of the above alcohol soluble protein gas-liquid interface self-assembled porous membrane, an active ingredient can be encapsulated and cross-linked, and its porous structure formed can intercept an active substance. The purpose of controlled release of the active substance can be achieved by using the alcohol soluble protein gas-liquid interface self-assembled porous membrane to load the active ingredient. Therefore, the present invention further seeks to protect a use of the above gas-liquid interface self-assembled porous membrane in preparation of an active substance controlled release product.

Compared with the prior art, the present invention has the following beneficial effects.

(1) The present invention provides a method for rapidly preparing an alcohol soluble protein interface self-assembled porous membrane by a one-step method, which has simple process and can be produced in a large scale, compared with a traditional solvent evaporation method for preparing a protein membrane (average consumed time is 4 hours), the preparation method is completed in 4 seconds, and the process efficiency is increased by 3,600 times, greatly improving the process efficiency.

(2) An alcohol soluble protein membrane product obtained by the present invention has a controllable porous structure. The structure (size, pore diameter, micro porosity) of the alcohol soluble protein interface self-assembled porous membrane can be precisely regulated and controlled by regulating and controlling process parameters, and a new preparation solution of an alcohol soluble protein base membrane, which is more efficient and has a modifiable structure compared with an alcohol soluble protein membrane prepared by a traditional solvent evaporation method, is developed.

DESCRIPTION OF THE EMBODIMENTS

The present invention is further illustrated below in combination with the appended drawings of the specification and specific implementations, but embodiments do not limit the present invention in any form. Unless otherwise specified, raw material reagents used in the embodiments of the present invention are conventionally purchased raw material reagents.

A test method for a pore diameter of an interface membrane: a microscopic morphology of the interface membrane is taken by a scanning electron microscope (SEM) under conditions of a 10.00 KV voltage and a 5.00 KX magnification, pore diameters in SEM pictures of different parts of the membrane are measured by imageJ software, firstly, a scale is set, the pictures are turned into gray, pore diameter sizes thereof are measured, five-point sampling is conducted, and multiple pore diameters are calculated to take an average value.

A test method for a porosity of an interface membrane: the porosity is defined as a ratio an area of pores to a total area of a material, ranging from 0 to 100%. The porosity of the material directly reflects the compactness of the material. The porosity thereof is measured by imageJ software. Firstly, a scale is set, pictures are turned into gray, the parts except the scale in the SEM pictures are frame-selected, a threshold is adjusted, pores are selected, and Measure is clicked to measure the porosity.

Figure 1:
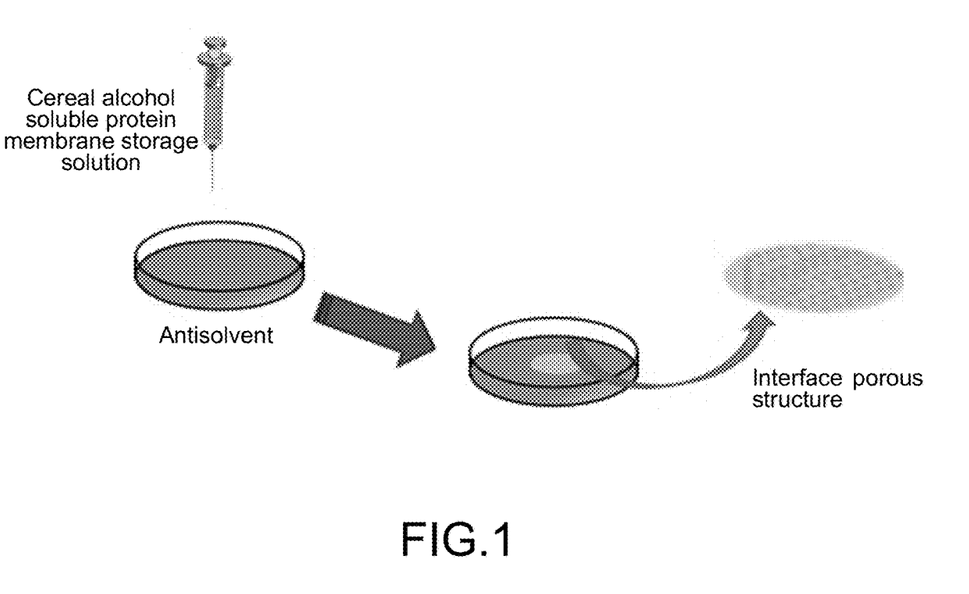
FIG. 1 shows a flow chart of preparing an alcohol soluble protein gas-liquid interface self-assembled porous membrane.

FIG. 1 is a flow chart of preparing an alcohol soluble protein gas-liquid interface self-assembled porous membrane.

Embodiment 1 Preparation of Interface Membrane by Zein Interface Self-Assembled One-Step Method (1) 2.0 g of zein was weighed to be added into 8.0 mL of an aqueous ethanol solution with a volume fraction of 80%, stirred and subjected to ultrasonic until the zein was completely dissolved, and a zein membrane storage solution with a mass fraction of 20% was prepared;

(2) 50 mL of a deionized water anti-solvent was taken, pH thereof was 5.2, and a temperature thereof was controlled to be 25° C.; and (3) one drop of the zein membrane storage solution obtained in the step (1) was dropped into the anti-solvent in the step (2) in 50 μL/drop to self-assemble to form a porous membrane.

Figure 2:
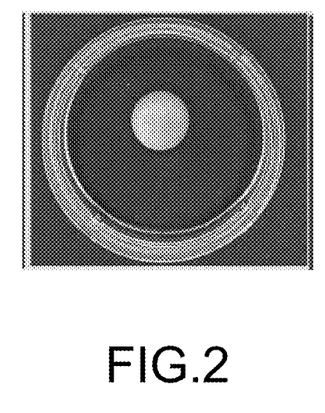
FIG. 2 shows a macro picture of an alcohol soluble protein gas-liquid interface self-assembled porous membrane prepared in Embodiment 1.

FIG. 2 shows an alcohol soluble protein gas-liquid interface self-assembled porous membrane prepared in this embodiment, membrane forming time is 3.0 seconds, an average pore diameter of the interface membrane is 2.36 μm, and a micro porosity of the membrane is 42.56%.

Embodiment 2 Preparation of Interface Membrane by Zein Interface Self-Assembled One-Step Method Same as Embodiment 1, a difference lied in that in step (1), a zein membrane storage solution with a mass fraction of 15% was prepared by an aqueous ethanol solution with a volume fraction of 80%.

Figure 3:
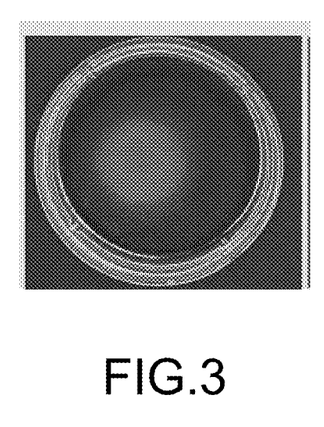
FIG. 3 shows a macro picture of an alcohol soluble protein gas-liquid interface self-assembled porous membrane prepared in Embodiment 2.

FIG. 3 shows an alcohol soluble protein gas-liquid interface self-assembled porous membrane prepared in this embodiment, membrane forming time is 3.0 seconds, an average pore diameter of the interface membrane is 2.67 μm, and a micro porosity of the membrane is 50.11%.

Embodiment 3 Preparation of Interface Membrane by Zein Interface Self-Assembled One-Step Method Same as Embodiment 1, a difference lied in that in step (1), a zein membrane storage solution with a mass fraction of 10% was prepared by an aqueous ethanol solution with a volume fraction of 80%.

Figure 4:
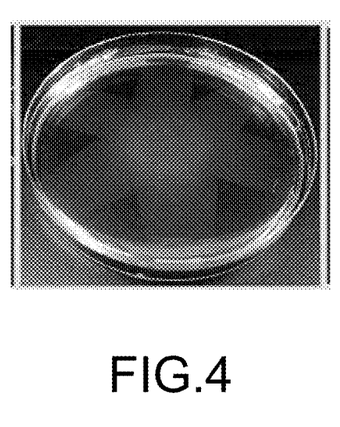
FIG. 4 shows a macro picture of an alcohol soluble protein gas-liquid interface self-assembled porous membrane prepared in Embodiment 3.

FIG. 4 shows an alcohol soluble protein gas-liquid interface self-assembled porous membrane prepared in this embodiment, membrane forming time is 3.0 seconds, a pore diameter of the interface membrane is 4.32 μm, and a micro porosity of the membrane is 63.16%.

Embodiment 4 Preparation of Interface Membrane by Zein Interface Self-Assembled One-Step Method Same as Embodiment 1, differences lied in that in step (1), a zein membrane storage solution with a mass fraction of 30% was prepared by an aqueous ethanol solution with a volume fraction of 80%; in step (2), a temperature of deionized water was controlled to be 40° C.

Membrane forming time of an alcohol soluble protein gas-liquid interface self-assembled porous membrane prepared in this embodiment was 2.5 seconds, a pore diameter of the interface membrane was 2.78 µm, and a micro porosity of the membrane was 52.67%.

Embodiment 5 Preparation of Interface Membrane by Zein Interface Self-Assembled One-Step Method Verifying an influence of different temperatures of an anti-solvent on membrane formation:

Same as Embodiment 1, a difference lied in that in step (2), temperatures of a deionized water anti-solvent were controlled to be 25° C., 30° C. and 40° C., respectively. Membrane forming time of obtained alcohol soluble protein gas-liquid interface self-assembled porous membranes was 3.0 seconds, 2.7 seconds and 1.8 seconds, respectively, pore diameters of the interface membranes were 2.36 µm, 1.52 µm and 0.74 µm, respectively, and micro porosities of the membranes were 42.56%, 37.37% and 28.37%.

Figure 5:
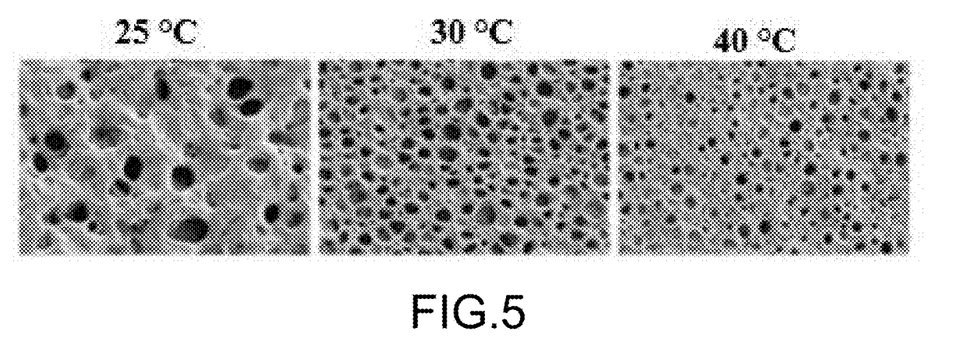
FIG. 5 shows microscopic morphology pictures of alcohol soluble protein gas-liquid interface self-assembled porous membranes obtained under conditions of different temperatures of an anti-solvent in Embodiment 5 under a scanning electron microscope.

FIG. 5 shows electron scanning microscope pictures of the alcohol soluble protein gas-liquid interface self-assembled porous membranes obtained under the anti-solvent at temperatures of 25° C., 30° C. and 40° C. It can be seen from FIG. 5 that by regulating and controlling the temperatures of the anti-solvent, the diffusion performance of zein can be changed, thereby affecting the microstructure of the interface membrane.

Embodiment 6 Preparation of Interface Membrane by Zein Interface Self-Assembled One-Step Method Verifying an influence of different concentrations of an aqueous ethanol solution as a zein good solvent on membrane formation:

Same as Embodiment 1, a difference lied in that in step (1), a zein was dissolved with 70% (v/v), 80% (v/v) and 90% (v/v) of an aqueous methanol solution, respectively. Membrane forming time of obtained alcohol soluble protein gas-liquid interface self-assembled porous membranes was 3.2 seconds, 3.0 seconds and 2.7 seconds, respectively, pore diameters of the interface membranes were 1.37 µm, 2.36 µm and 3.17 µm, respectively, and micro porosities of the membranes were 30.15%, 42.56% and 48.36%.

Figure 6:
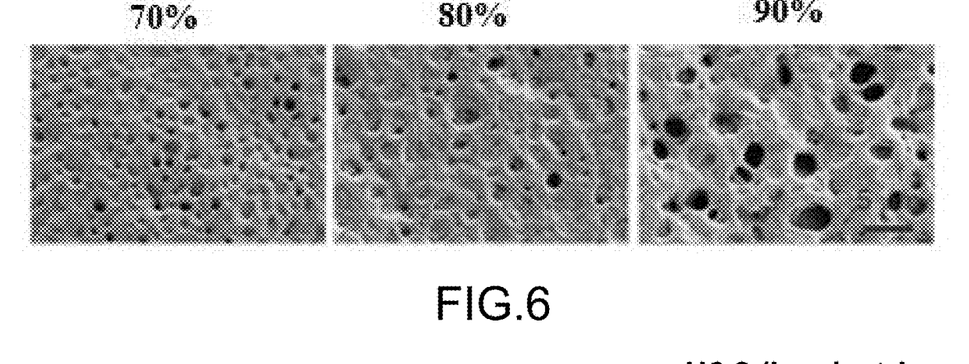
FIG. 6 shows microscopic morphology pictures of alcohol soluble protein gas-liquid interface self-assembled porous membranes prepared by using different concentrations of an aqueous ethanol solution as a zein good solvent in Embodiment 6 under a scanning electron microscope.

FIG. 6 shows pictures of the alcohol soluble protein gas-liquid interface self-assembled porous membranes prepared by using different concentrations of an aqueous ethanol solution as a zein good solvent. It can be seen from FIG. 6 that by regulating and controlling the concentrations of the good solvent, the diffusion performance of zein at an interface can be changed, the reason is that the zein contains more than 50% hydrophobic amino acids, with the increase of the ethanol concentration of the good solvent, the solubility of the zein increases, which affects the diffusion of the zein at the interface, thus affecting the microstructure of the interface membrane.

Embodiment 7 Preparation of Interface Membrane by Zein Interface Self-Assembled One-Step Method Verifying an influence of different pH of an anti-solvent on membrane formation:

Same as Embodiment 1, a difference lied in that pH of a deionized water anti-solvent was regulated to be 3.0, 5.2, 6.2 (isoelectric point), 7.0 and 9.0 by sodium hydroxide and/or hydrogen chloride, respectively.

Membrane forming time of obtained alcohol soluble protein gas-liquid interface self-assembled porous membranes was 3.2 seconds, 3.0 seconds, 2.9 seconds, 3.1 seconds and 3.5 seconds, respectively, pore diameters of the interface membranes were 2.15 µm, 2.36 µm, 2.47 µm, 1.96 µm and 2.17 µm, respectively, and micro porosities of the membranes were 45.32%, 42.56%, 34.56%, 45.67% and 43.23%.

Figure 7:
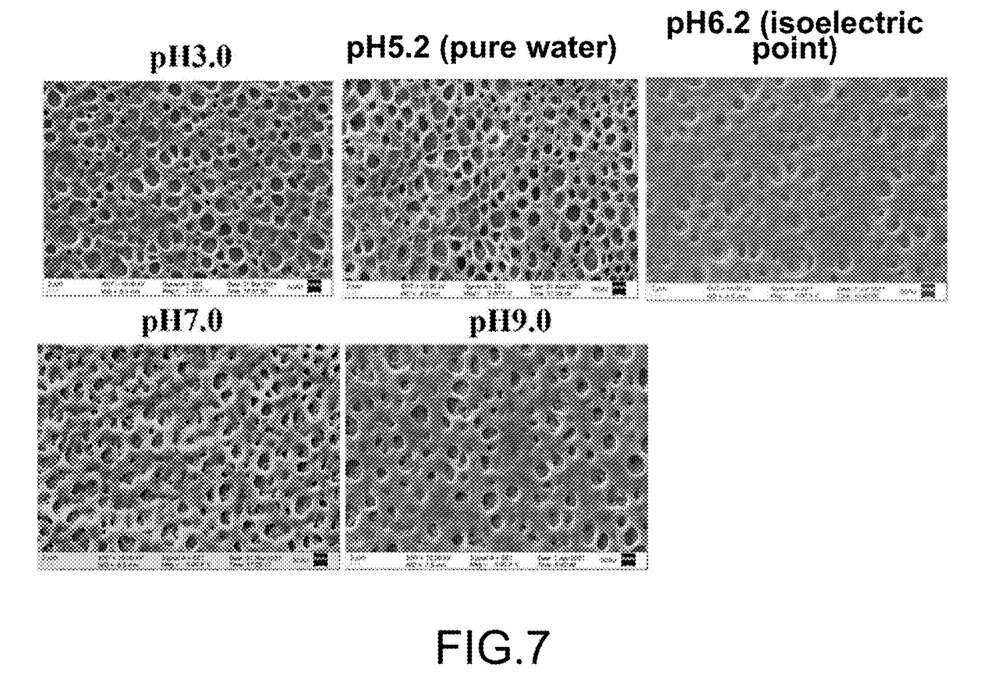
FIG. 7 shows microscopic morphology pictures of alcohol soluble protein gas-liquid interface self-assembled porous membranes prepared by different pH of an anti-solvent in Embodiment 7 under a scanning electron microscope.

FIG. 7 shows SEM pictures of alcohol soluble protein gas-liquid interface self-assembled porous membranes prepared by different pH of an anti-solvent. It can be seen from FIG. 7 that by regulating and controlling the pH of the anti-solvent, the self-aggregation speed of zein in the anti-solvent can be changed, the pH in the anti-solvent will affect the solubility of zein molecules, and under an acidic condition, the zein has low solubility, fast self-aggregation and slow diffusion; the isoelectric point pH6.2 has no charge effect, self-aggregation is fast and diffusion is slow; under an alkaline condition, the solubility of the zein increases, the self-aggregation speed decreases, and the diffusion performance increases, thereby affecting the microstructure of the interface membrane.

Embodiment 8 Preparation of Interface Membrane by Zein Interface Self-Assembled One-Step Method Verifying an influence of different ionic strengths of an anti-solvent on membrane formation:

Same as Embodiment 1, a difference lied in that an ionic strength of a deionized water anti-solvent was regulated to be 50 mM, 100 mM, 200 mM and 500 mM by sodium chloride.

Membrane forming time of obtained alcohol soluble protein gas-liquid interface self-assembled porous membranes was 2.5 seconds, 2.6 seconds, 3.0 seconds and 3.5 seconds, respectively, pore diameters of the interface membranes were 1.83 µm, 0.51 µm, 0.34 µm and 0.21 µm, respectively, and micro porosities of the membranes were 42.31%, 23.11%, 15.22% and 6.37%. A contact angle of an upper surface of the zein interface membrane prepared in this embodiment was larger than that of a lower surface thereof.

Figure 8:
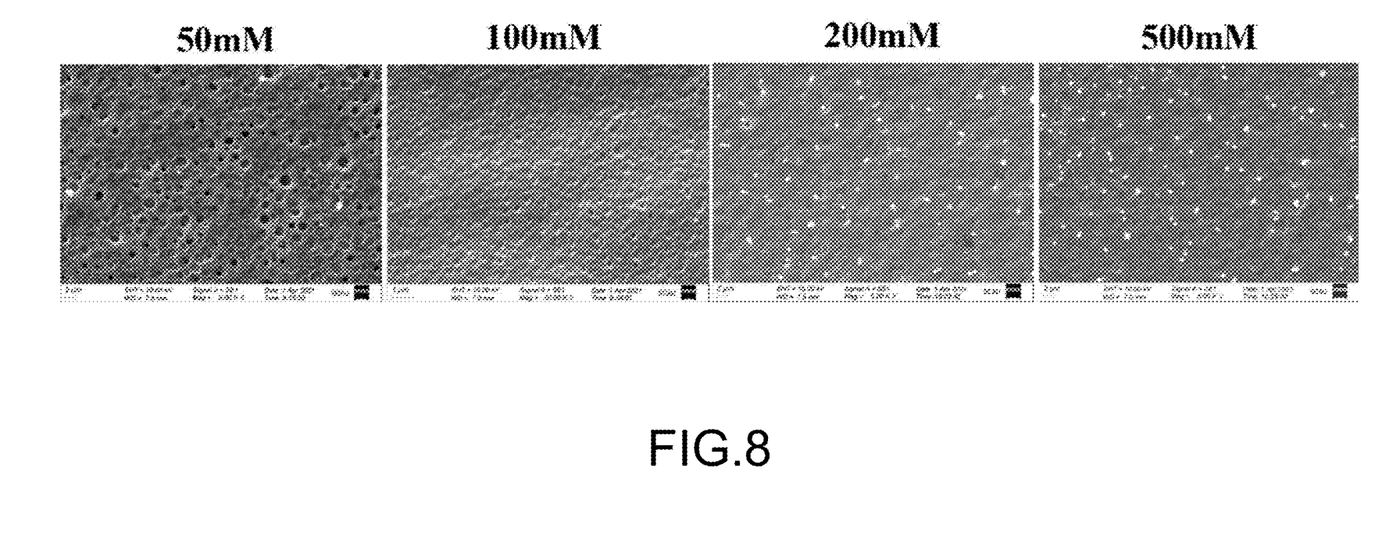
FIG. 8 shows microscopic morphology pictures of alcohol soluble protein gas-liquid interface self-assembled porous membranes prepared by different ionic strengths of an anti-solvent in Embodiment 8 under a scanning electron microscope.

FIG. 8 shows pictures of the alcohol soluble protein gas-liquid interface self-assembled porous membranes prepared by different ionic strengths of the anti-solvent. It can be seen from FIG. 8 that by regulating and controlling the ionic strength of the anti-solvent, the interaction force between protein molecules can be regulated and controlled, and the self-aggregation performance of zein can be changed, thereby affecting the microstructure of the interface membrane.

Embodiment 9 Preparation of Interface Membrane by Gliadin Interface Self-Assembled One-Step Method Same as Embodiment 1, a difference lied in that the zein was replaced with gliadin.

Membrane forming time of an alcohol soluble protein gas-liquid interface self-assembled porous membrane prepared in this embodiment was 3.2 seconds, a pore diameter of the interface membrane was 2.19 µm, and a micro porosity of the membrane was 33.56%.

Embodiment 10 Preparation of Interface Membrane by Kafirin Interface Self-Assembled One-Step Method Same as Embodiment 1, a difference lied in that the zein was replaced with kafirin.

Membrane forming time of an alcohol soluble protein gas-liquid interface self-assembled porous membrane prepared in this embodiment was 3.0 seconds, a pore diameter of the interface membrane was 2.47 μm, and a micro porosity of the membrane was 42.11%.

Embodiment 11 Preparation of Interface Membrane by Hordein Interface Self-Assembled One-Step Method Same as Embodiment 1, a difference lied in that the zein was replaced with hordein.

Membrane forming time of an alcohol soluble protein gas-liquid interface self-assembled porous membrane prepared in this embodiment was 3.1 seconds, a pore diameter of the interface membrane was 2.17 μm, and a micro porosity of the membrane was 36.23%.

Embodiment 12 Preparation of Interface Membrane by Zein Interface Self-Assembled One-Step Method Same as Embodiment 1, a difference lied in that in step (1), a zein was dissolved with 80% (v/v) of an aqueous methanol solution.

Membrane forming time of an alcohol soluble protein gas-liquid interface self-assembled porous membrane prepared in this embodiment was 2.3 seconds, a pore diameter of the interface membrane was 2.58 μm, and a micro porosity of the membrane was 48.45%.

Embodiment 13 Preparation of Interface Membrane by Zein Interface Self-Assembled One-Step Method Same as Embodiment 1, a difference lied in that in step (1), a zein was dissolved with 80% (v/v) of an aqueous acetic acid solution.

Membrane forming time of an alcohol soluble protein gas-liquid interface self-assembled porous membrane prepared in this embodiment was 2.1 seconds, a pore diameter of the interface membrane was 3.34 μm, and a micro porosity of the membrane was 42.11%.

Embodiment 14 Preparation of Interface Membrane by Zein Interface Self-Assembled One-Step Method Same as Embodiment 1, a difference lied in that in step (1), a zein was dissolved with 80% (v/v) of an aqueous acetone solution.

Membrane forming time of an alcohol soluble protein gas-liquid interface self-assembled porous membrane prepared in this embodiment was 3.0 seconds, a pore diameter of the interface membrane was 2.18 μm, and a micro porosity of the membrane was 35.67%.

Embodiment 15 Preparation of Interface Membrane by Zein Interface Self-Assembled One-Step Method Same as Embodiment 11, a difference lied in that in step (2), 20% (v/v) of an aqueous methanol solution was used as an anti-solvent, pH thereof was regulated to be 5.2 by sodium hydroxide and/or hydrogen chloride, and a temperature thereof was controlled to be 25° C.

Membrane forming time of an alcohol soluble protein gas-liquid interface self-assembled porous membrane prepared in this embodiment was 2.5 seconds, a pore diameter of the interface membrane was 1.75 μm, and a micro porosity of the membrane was 33.21%.

Embodiment 16 Preparation of Interface Membrane by Zein Interface Self-Assembled One-Step Method Same as Embodiment 12, a difference lied in that in step (2), 20% (v/v) of an aqueous acetic acid solution was used as an anti-solvent, pH thereof was regulated to be 5.2 by sodium hydroxide and/or hydrogen chloride, and a temperature thereof was controlled to be 25° C. Membrane forming time of an alcohol soluble protein gas-liquid interface self-assembled porous membrane prepared in this embodiment was 3.0 seconds, a pore diameter of the interface membrane was 1.98 μm, and a micro porosity of the membrane was 43.21%.

Embodiment 17 Preparation of Interface Membrane by Zein Interface Self-Assembled One-Step Method Same as Embodiment 13, a difference lied in that in step (2), 20% (v/v) of an aqueous acetone solution was used as an anti-solvent, pH thereof was regulated to be 5.2 by sodium hydroxide and/or hydrogen chloride, and a temperature thereof was controlled to be 25° C.

Membrane forming time of an alcohol soluble protein gas-liquid interface self-assembled porous membrane prepared in this embodiment was 3.0 seconds, a pore diameter of the interface membrane was 1.23 μm, and a micro porosity of the membrane was 36.11%.

Comparative Example 1

Same as Embodiment 1, a difference lied in that in step (1), a zein membrane storage solution with a mass fraction of 5% was prepared by an aqueous ethanol solution with a volume fraction of 80%.

Figure 9:
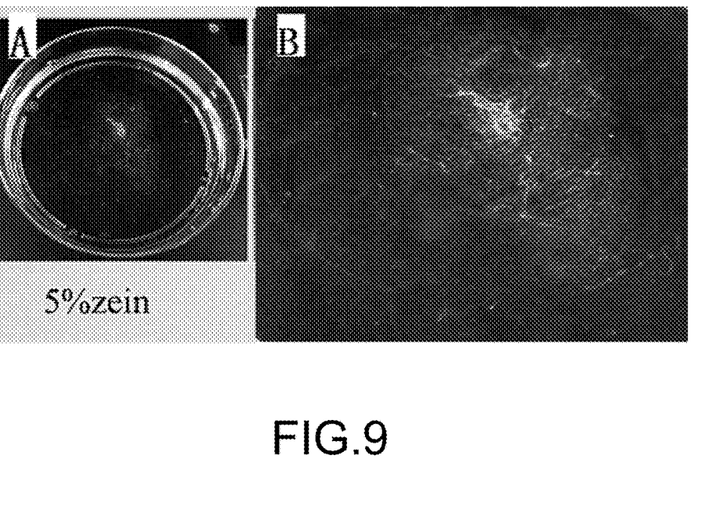
FIG. 9 shows a macro picture of an alcohol soluble protein membrane prepared in Comparative Example 1.

In FIG. 9, picture A is a picture of a preparation process of this comparative example, and a membrane cannot be formed at an interface by the method of this comparative example, indicating that the interface membrane needs a certain concentration of cereal alcohol soluble protein to form a thin membrane on the interface. In FIG. 9, picture B is a macro picture of zein at an interface, and it can be seen that a 5% zein membrane storage solution cannot form a continuous thin membrane.

Comparative Example 2

Same as Embodiment 1, a difference lied in that in step (1), a zein membrane storage solution with a mass fraction of 50% was prepared by an aqueous ethanol solution with a volume fraction of 80%.

The zein membrane storage solution prepared in this comparative example has low solubility and high viscosity and is titrated by an anti-solvent, the solution cannot diffuse at an interface and a thin membrane cannot be formed.

Comparative Example 3

Same as Embodiment 1, a difference lied in that in step (2), a temperature of an anti-solvent was controlled to be 10° C.

Figure 10:
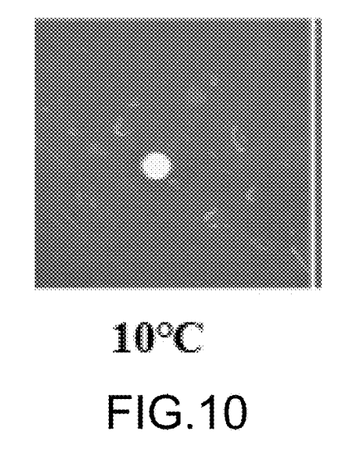
FIG. 10 shows a macro picture of an alcohol soluble protein membrane prepared in Comparative Example 3.

FIG. 10 shows a thin membrane prepared in this comparative example. It can be seen that when the temperature is too low, zein is difficult to diffuse at an interface, and the diameter of the thin membrane formed is very small and is 0.15 cm.

Comparative Example 4

Same as Embodiment 1, a difference lied in that in step (2), a temperature of an anti-solvent was controlled to be 20° C.

Figure 11:
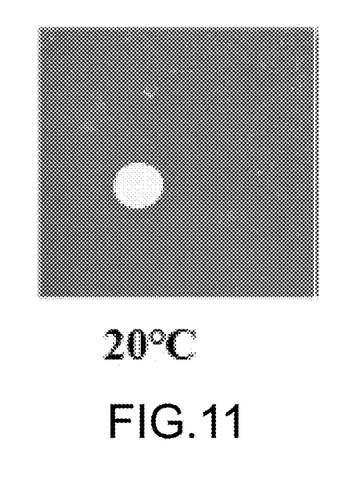
FIG. 11 shows a macro picture of an alcohol soluble protein membrane prepared in Comparative Example 4.

FIG. 11 shows a thin membrane prepared in this comparative example. It can be seen that when the temperature is relatively low, the diameter of the thin membrane formed by zein at an interface is 0.22 cm, which is larger than that at 10° C., but the whole membrane solution is difficult to diffuse at the interface.

Comparative Example 5

Same as Embodiment 1, a difference lied in that in step (2), a temperature of an anti-solvent was controlled to be 50° C.

The membrane diameter formed of a thin membrane prepared by the method in this comparative example is very large and is 4.3 cm, but the membrane cannot be uncovered, because zein molecules diffuse too quickly at an interface and can form a membrane within 2 seconds, but the formed membrane cannot be uncovered.

Comparative Embodiment 6 Preparation of Zein Membrane by Tape Casting Method

Other conditions were the same as those in Embodiment 1. Differences lied in that instead of titration by an anti-solvent, a zein membrane storage solution was poured into a flat plate, and zein self-assembled to form a thin membrane by solvent evaporation. The film forming time of the method was up to 4 hours, and the ethanol consumption was large and was 1 L ethanol/m 2 thin membrane.

Comparative Embodiment 7 Preparation of Zein Membrane by Pressed-Disc Method

Other conditions were the same as those in Embodiment 1. Differences lied in that instead of titration by an anti-solvent, an extrudate was cut into small pellets by a granulator, the small pellets were dried by hot air, extruded granules were then extruded into sheets by secondary extrusion, and finally, a mixed membrane forming material was blown into a thin membrane by a blown thin membrane extruder. The method has many operation steps, and the prepared membrane has single modifiability.

Experimental Example 1

In order to investigate the change of the morphology and structure of a self-assembled interface membrane by different cereal alcohol soluble protein concentrations, interface membranes obtained in Embodiment 2 and Embodiment 3 were tested, and after uncovered, the membranes were dried in a constant temperature and humidity drying oven for 48 hours, and characterized by an SEM.

Figure 12:
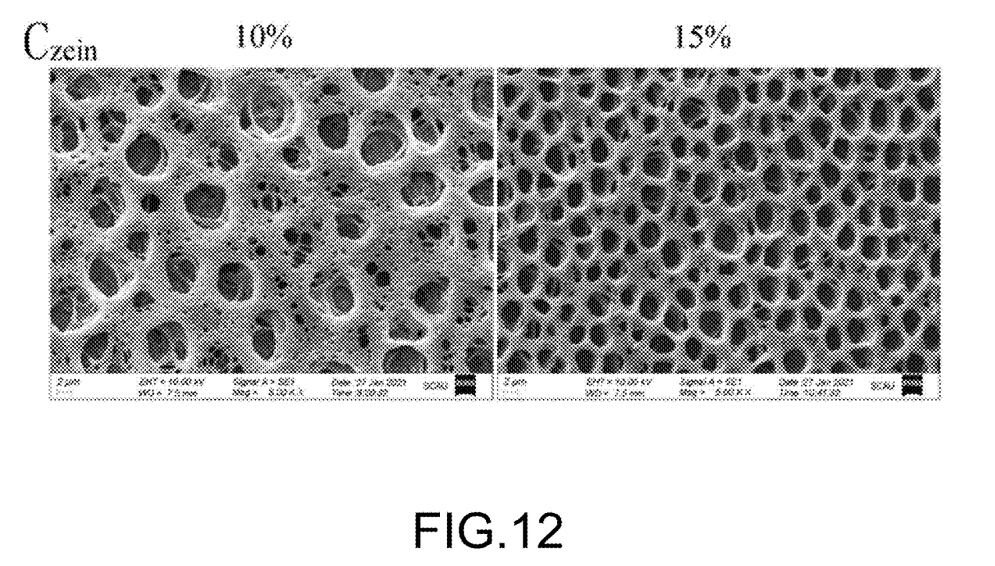
FIG. 12 shows microscopic morphology pictures of alcohol soluble protein gas-liquid interface self-assembled porous membranes obtained in Embodiment 2 and Embodiment 3 under a scanning electron microscope.

FIG. 12 shows scanning electron microscope pictures of interface membranes obtained in Embodiment 2 and Embodiment 3. It can be seen from the pictures that micro pore structures are different greatly when zein concentrations are 10% and 15%. A pore diameter at 15% is slightly smaller than that at 10%, a pore layered structure of an interface membrane formed by a 10% zein solution is relatively obvious, a pore structure of an interface membrane formed by a 15% zein solution is relatively medium, and the reason is that there are protein self-aggregation and solvent diffusion in the interface self-assembly process of zein, the number of protein molecules of different concentrations of protein and solution viscosity are different, so the aggregation degree and diffusion will change. The viscosity under the 10% zein solution is less than that under the 15% zein solution, so the 10% zein solution diffuses relatively rapidly at the interface, and formed pores are relatively large and are layered. From the above structure analysis, it can be concluded that the structure of the alcohol soluble protein interface membrane can be regulated and controlled by the concentration of alcohol soluble protein.

Experimental Example 2

In order to verify the regulatory effect of a pH value of an anti-solvent on the structure of a cereal alcohol soluble protein membrane, the protein membrane obtained in Embodiment 6 was tested, and after the membrane was uncovered, a diameter thereof was measured with a vernier caliper.

Figure 13:
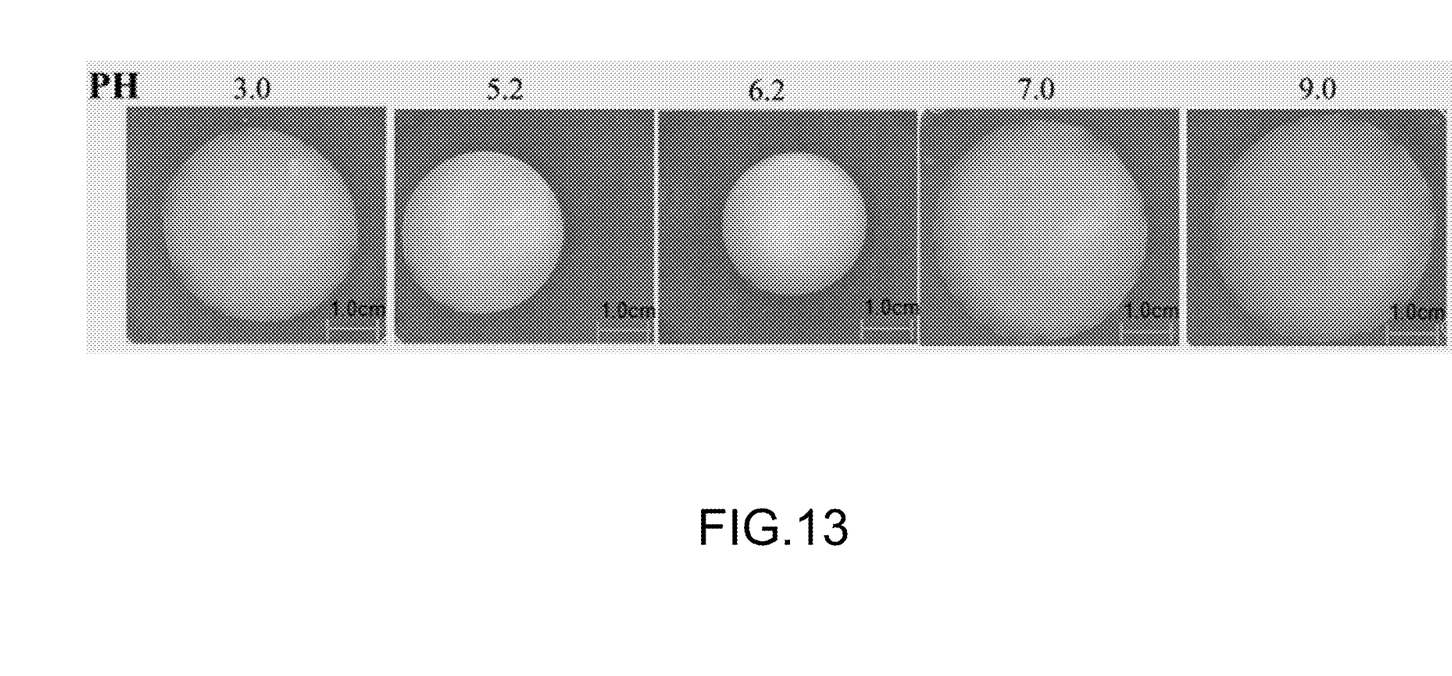
FIG. 13 shows diameter test of an alcohol soluble protein gas-liquid interface self-assembled porous membrane obtained in Embodiment 7.

FIG. 13 shows diameter results of protein membranes obtained in Embodiment 6. It can be seen from the figure that the minimum diameter of the pH6.2 (isoelectric point) membrane is 2.74 cm, the diameters of the membranes under an acidic condition (pH3.0), a neutral condition (pH7.0) and an alkaline condition (pH9.0) are all large and are 3.62 cm, 3.84 cm and 4.10 cm, respectively, and the diameter of the membrane under a pure water condition (pH5.2) is 3.51 cm. The reason is that at the isoelectric point, a net charge between molecules is zero, the interaction between molecules is weakened, and the self-aggregation ability is enhanced, so that the diameter of the membrane is decreased; when the protein is under the acidic, neutral or alkaline pH value, surfaces of the protein molecules carry a large amount of charge, and the protein molecules interact with each other and the interiors of the molecules interact with each other, the protein molecules stretch, which increases the diameter of the interface membrane, under the pure water condition, there is no influence of external ions, and a protein stock solution diffuses at the interface depending on the concentration gradient of the solution to form the interface membrane.

Experimental Example 3

Figure 14:
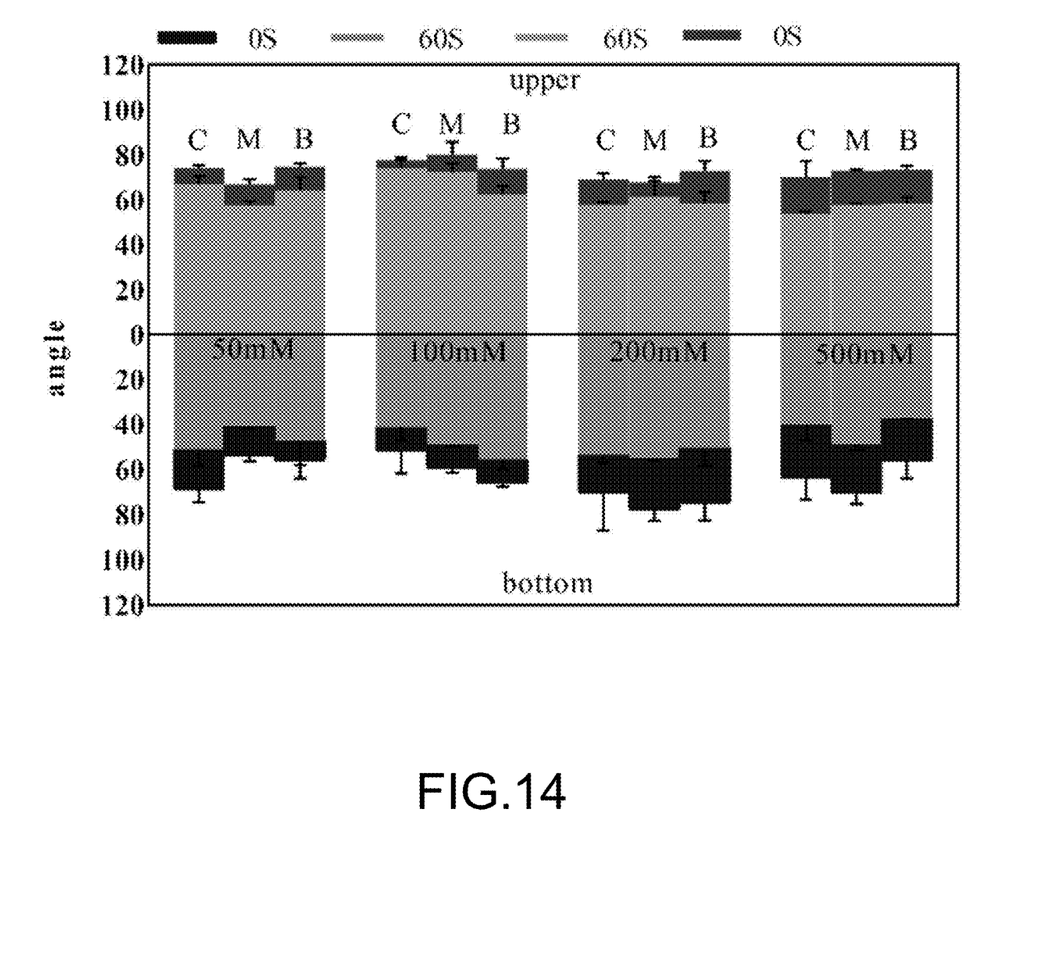
FIG. 14 shows contact angle test results of an alcohol soluble protein gas-liquid interface self-assembled porous membrane obtained in Embodiment 8.

In order to study the changes in hydrophilicity and hydrophobicity of upper and lower surfaces of a cereal alcohol soluble protein interface membrane due to different contact interfaces, the cereal alcohol soluble protein interface membrane obtained in Embodiment 7 was tested, after uncovered, the membrane was dried in a constant temperature and humidity drying oven for 48 hours, the hydrophilicity and hydrophobicity of the upper and lower surfaces of the membrane as well as from the surface center of the membrane to the edge for 0 second and 60 seconds were characterized by a water contact angle (WCA), and characterization results were shown in FIG. 14.

It can be seen from FIG. 14 that, under different salt ion conditions of an anti-solvent, on the whole, the contact angle of the upper surface is between 60 and 80 and the contact angle of the lower surface is between 40 and 60, so the lower surface is more hydrophilic than the upper surface overall. The lower surface is in contact with water, and there are many hydrophilic groups exposed during self-assembly, meanwhile, the addition of salt ions in the anti-solvent will affect the speed of protein self-assembly, thus changing the micro morphology and structure of the membrane surface, and the protein on the lower surface will combine with the salt ions in the anti-solvent during self-assembly, and the dissolution of the salt ions will also decrease the contact angle. Therefore, it can be concluded that by changing the ionic strength of the anti-solvent, the hydrophilic and hydrophobic groups and the microscopic morphology and structure of the surface of the interface membrane can be precisely regulated and controlled.

Obviously, the above embodiments of the present invention are only instances for clearly illustrating the present invention, rather than limiting the implementations of the present invention. For those of ordinary skill in the art, changes or modifications in other different forms may also be made on the basis of the above illustration. There is no need and cannot be exhaustive of all embodiments here. Any amendment, equivalent replacement, improvement, etc., made within the spirit and principle of the present invention should be included within the scope of protection claimed by the present invention.

What is claimed is:

1. A method for preparing an alcohol soluble protein gas-liquid interface self-assembled porous membrane, comprising the following steps:

S1, adding an alcohol soluble protein into a good solvent to be dissolved to obtain a membrane storage solution with an alcohol soluble protein concentration of 10 to 30 wt %;

S2, regulating and controlling a temperature of an anti-solvent to be 25° C. to 40° C.; and S3, dropping the membrane storage solution in the S1 into the anti-solvent in the S2 to form a self-assembled porous membrane;

wherein pH of the anti-solvent is 3.0 to 10.0, and an ionic strength thereof is 0 to 700 mM;

wherein the good solvent comprises any one of 50% to 90% (v/v) of an aqueous ethanol solution, 60% to 90% (v/v) of an aqueous methanol solution, 60% to 100% (v/v) of an aqueous acetic acid solution and 70% to 90% (v/v) of an aqueous acetone solution; wherein 100% (v/v) of the aqueous acetic acid solution means a pure acetic acid;

wherein the anti-solvent comprises any one of water, 0.1% to 50% (v/v) of an aqueous ethanol solution, 0.1% to 60% (v/v) of an aqueous methanol solution, 0.1% to 60% (v/v) of an aqueous acetic acid solution and 0.1% to 70% (v/v) of an aqueous acetone solution;

titration of the anti-solvent in the S3 is single titration, and a volume ratio of the membrane storage solution to the anti-solvent during titration is 1:(500 to 10,000).

2. The method according to claim 1, wherein the alcohol soluble protein comprises any one of gliadin, zein, kafirin and hordein.

3. An alcohol soluble protein gas-liquid interface self-assembled porous membrane prepared by the method of claim 1.

4. An alcohol soluble protein gas-liquid interface self-assembled porous membrane prepared by the method of claim 2.

* * * * *